United States Patent
Rudolph

(10) Patent No.: US 10,682,025 B2
(45) Date of Patent: Jun. 16, 2020

(54) PORTABLE URINAL

(71) Applicant: Linda Rudolph, Littleton, CO (US)

(72) Inventor: Linda Rudolph, Littleton, CO (US)

( * ) Notice: Subject to any disclaimer, the term of this patent is extended or adjusted under 35 U.S.C. 154(b) by 0 days.

(21) Appl. No.: 15/474,545

(22) Filed: Mar. 30, 2017

(65) Prior Publication Data

US 2017/0325641 A1  Nov. 16, 2017

Related U.S. Application Data

(60) Provisional application No. 62/334,503, filed on May 11, 2016.

(51) Int. Cl.
*A47K 11/12*  (2006.01)
*A61F 5/455*  (2006.01)

(52) U.S. Cl.
CPC ............ *A47K 11/12* (2013.01); *A61F 5/4556* (2013.01)

(58) Field of Classification Search
CPC ............... A47K 11/12; A47K 17/02; A61G 9/003–006; A47B 2095/021–024; A47B 2095/027; E05B 2001/0023; E05B 1/003; A61F 5/4556
USPC ......... 16/408–409, 417–420; 4/144.1–144.4, 4/450–458, 460
See application file for complete search history.

(56) References Cited

U.S. PATENT DOCUMENTS

| | | | |
|---|---|---|---|
| 2,697,244 A * | 12/1954 | Lincke | A47B 95/02 16/419 |
| 3,349,768 A * | 10/1967 | Keane | A61F 5/455 604/329 |
| 3,699,612 A * | 10/1972 | Hanley | A47B 95/02 16/405 |
| 4,187,562 A * | 2/1980 | Mioduski | A61G 9/006 4/144.3 |
| 4,189,804 A * | 2/1980 | Flowerday | A47B 95/02 16/419 |
| 4,427,270 A * | 1/1984 | Kraft | G02B 21/24 359/368 |
| 4,496,355 A * | 1/1985 | Hall | F16K 15/144 604/327 |
| 4,531,245 A * | 7/1985 | Lowd | A47K 11/00 141/337 |
| 4,568,339 A | 2/1986 | Steer | |
| 5,079,788 A * | 1/1992 | Raupp | A61G 9/003 4/450 |
| 5,487,393 A * | 1/1996 | Haswell | A61B 10/007 600/549 |

(Continued)

FOREIGN PATENT DOCUMENTS

GB  720629  * 12/1954  ............ A61G 9/003

*Primary Examiner* — David P Angwin
*Assistant Examiner* — Nicholas A Ros
(74) *Attorney, Agent, or Firm* — Boudwin Intellectual Property; Daniel Boudwin

(57) ABSTRACT

A portable female urinal. The portable female urinal includes a container having a front side, a back side, a first sidewall, a second sidewall, a base, and an upper end defining an interior volume. The first and second sidewalls bow inwards to create a saddle shape. An aperture is included within the upper end that is configured to receive urine. A telescopic spout having an extended and collapsed position is included on the front side. The telescopic spout is designed to access the interior volume such that the contents of the container can be evacuated therethrough.

14 Claims, 4 Drawing Sheets

(56) References Cited

U.S. PATENT DOCUMENTS

| | | | | |
|---|---|---|---|---|
| 6,021,529 A * | 2/2000 | Abbato | ............... | A61G 9/006 |
| | | | | 4/144.1 |
| 6,299,606 B1 * | 10/2001 | Young | ............... | A61B 10/007 |
| | | | | 604/317 |
| 6,338,166 B1 | 1/2002 | Hereford | | |
| 7,363,661 B1 * | 4/2008 | Myers | ............... | A47K 11/12 |
| | | | | 4/144.1 |
| 8,015,627 B2 * | 9/2011 | Baker | ............... | A61G 9/006 |
| | | | | 222/464.7 |
| 8,337,477 B2 | 12/2012 | Parks et al. | | |
| 8,640,913 B2 * | 2/2014 | Berendes | ............ | A45C 13/26 |
| | | | | 16/409 |
| 8,650,669 B1 * | 2/2014 | Kolter | ............... | A47K 11/12 |
| | | | | 4/144.1 |
| 8,800,071 B2 * | 8/2014 | Sanchez Moreno | ... | A61G 9/003 |
| | | | | 4/452 |
| 8,850,631 B2 * | 10/2014 | Stekloff | ............. | A61G 9/003 |
| | | | | 4/455 |
| 9,339,409 B2 * | 5/2016 | Brathwaite | ........ | A61F 5/4556 |
| 2008/0083060 A1 * | 4/2008 | Beers | ............... | A61G 9/003 |
| | | | | 4/455 |
| 2009/0048569 A1 | 2/2009 | Salehi | | |
| 2012/0210503 A1 | 8/2012 | Anzivino et al. | | |
| 2013/0239311 A1 | 9/2013 | Valenti | | |

* cited by examiner

PORTABLE URINAL

CROSS REFERENCE TO RELATED APPLICATIONS

This application claims the benefit of U.S. Provisional Application No. 62/334,503 filed on May 11, 2016. The above identified patent application is herein incorporated by reference in its entirety to provide continuity of disclosure.

BACKGROUND OF THE INVENTION

The present invention relates to portable urinals. More specifically, the present invention relates to a portable urinal with a telescopic spout designed for female use adapted to be easily emptied and cleaned.

Many people enjoy spending time out of the house, however in many situations, a restroom is not available, such as while driving or in the wilderness and the like. Without access to a restroom, it can be difficult to relieve oneself in privacy, especially for females. While some portable urinals designed to be used by females exist, they tend to be bulky and difficult to clean. Additionally, they are not designed to be used in a standing position, which may be required based upon the location of the user.

In light of the devices disclosed in the known art, it is submitted that the present invention substantially diverges in design elements from the known art and consequently it is clear that there is a need in the art for an improvement to existing portable urinals designed for female use. In this, regard, the instant invention substantially fulfills these needs.

SUMMARY OF THE INVENTION

In view of the foregoing disadvantages inherent in the known types of portable urinals now present in the prior art, the present invention provides a portable urinal wherein the same can be utilized for providing convenience for the user when relieving oneself of urine while standing.

The present system comprises a container having a front side, a back side, a first sidewall, a second sidewall, a base, and an upper end creating an interior volume. The first and second sidewalls bow inwards to create a saddle shape. An aperture is located within the upper end configured to receive urine therethrough. A telescopic spout is disposed on one of the back side and front side. In some embodiments, the telescopic spout is adapted to rest flush with the container when in its collapsed position. Some embodiments of the portable female urinal include a cap to create a watertight seal at the end of the telescopic spout. Further embodiments comprise a handle having an outer surface disposed on one of the front side and the back side. In some embodiments, in the handle's resting position, the outer surface is flush with the container. Further embodiments include a hinge connecting the base to the container such that the base can open about the hinge. Such embodiments also include a latch mechanism along the side opposite the hinge to secure the base in a closed position.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
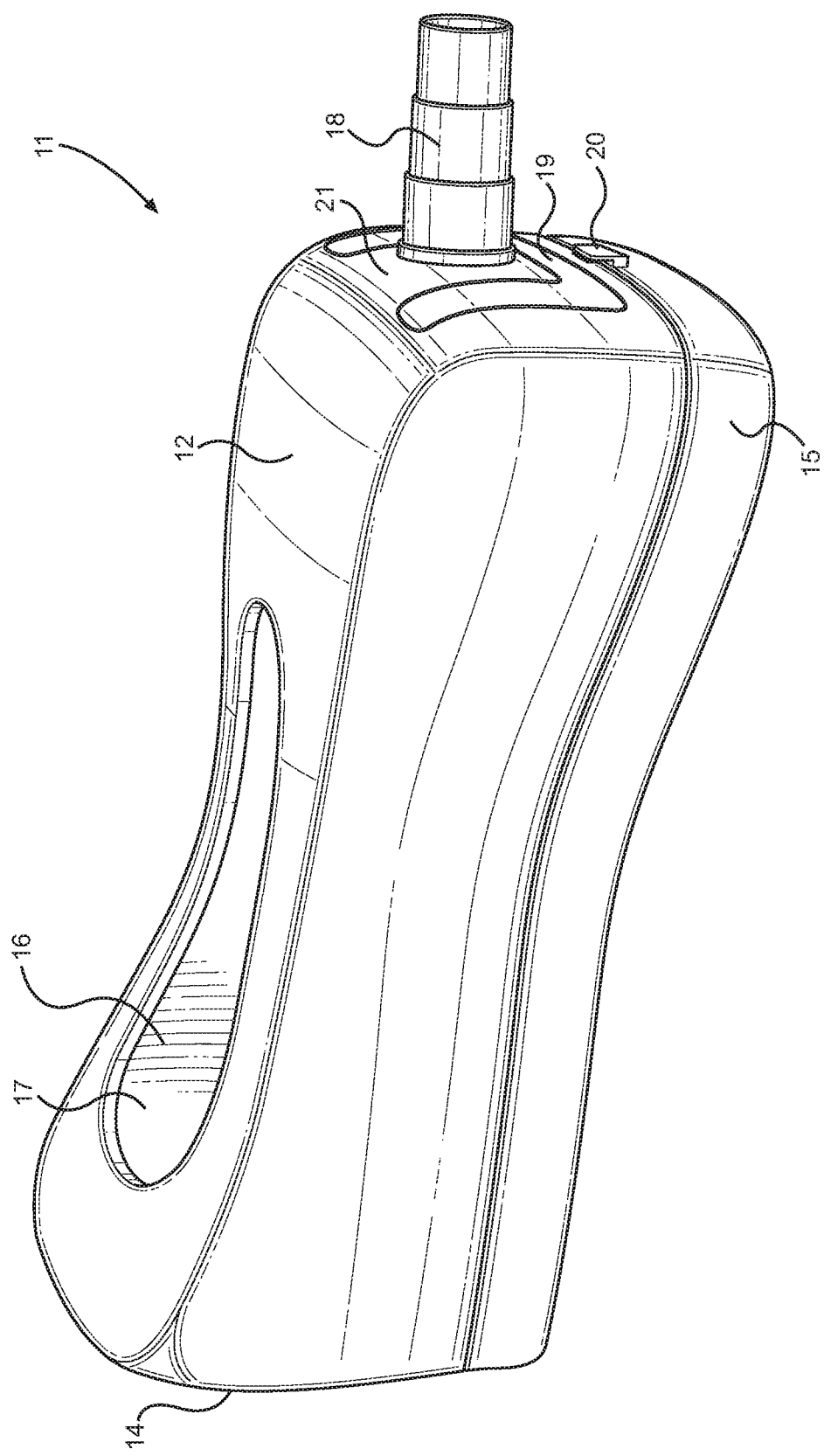
FIG. 1 shows a perspective view of an embodiment of the portable urinal.

Reference is made herein to the attached drawings. Like reference numerals are used throughout the drawings to depict like or similar elements of the portable urinal. The figures are intended for representative purposes only and should not be considered to be limiting in any respect.

Figure 2:
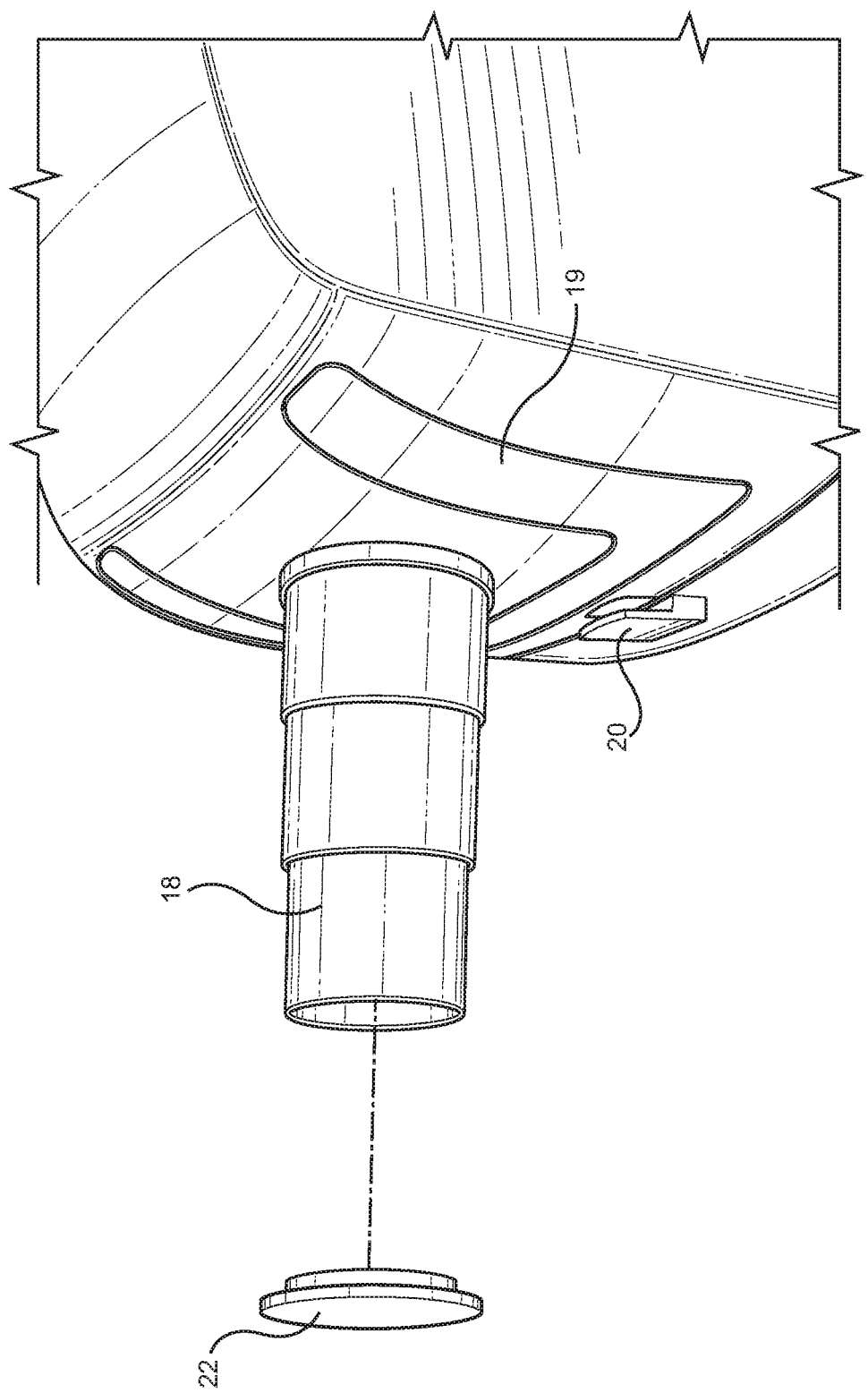
FIG. 2 shows a close-up view of an embodiment of the telescopic spout of the portable urinal.

Referring now to FIGS. 1 and 2, there is shown a perspective view of an embodiment of the portable urinal and a close-up view of an embodiment of the telescopic spout of the portable urinal, respectively. The container 11 comprises a first sidewall 13, a second sidewall 30, an upper end 12, a base 15, a front end 21, and a back end 14, defining an interior volume 17. An aperture 16 is disposed on the upper end 12 and is configured to receive urine therethrough. In the illustrated embodiment, the aperture 16 has a perimeter similar to the perimeter of the container 11 in order to provide a large enough aperture 16 to minimize spillage. In the illustrated embodiment, the first and second sidewalls 13, 30 bow inwards towards the interior volume 17 such that the first and second sidewalls 13, 30 define a narrower middle section having a smaller cross sectional area than the front and back ends, 21, 14. This creates a saddle shape adapted to provide a comfortable grip for the user to hold the container 11 between the user's thighs. In the illustrated embodiment, the back end 14 includes a height greater than the height of the front end 21. In this way, the back end 14 contours to the general shape of a user and guides the user, as it assists with alignment over the aperture.

A spout 18 is disposed along the front end 21 such that the contents of the interior volume 17 can be evacuated from the container 11 therethrough. In the illustrated embodiment, the spout 18 is in its extended position, however, in other embodiments, the spout 18 is configured to be telescopic allowing the spout 18 to collapse such that the spout 18 is flush with the front end 21. This allows the container 11 to comprise a more compact shape, aiding in portability. In the illustrated embodiment of FIG. 2, there is shown a cap 22 that removably secures to the end of the spout 18 such that a watertight seal is formed. In the illustrated embodiment of FIG. 2, the cap 22 removably secures to the end of the spout 18 via a compression fit. In alternative embodiments, the cap 22 is externally threaded to engage with internal threats of the spout 18 to removably secure to the spout 18.

Figure 3:
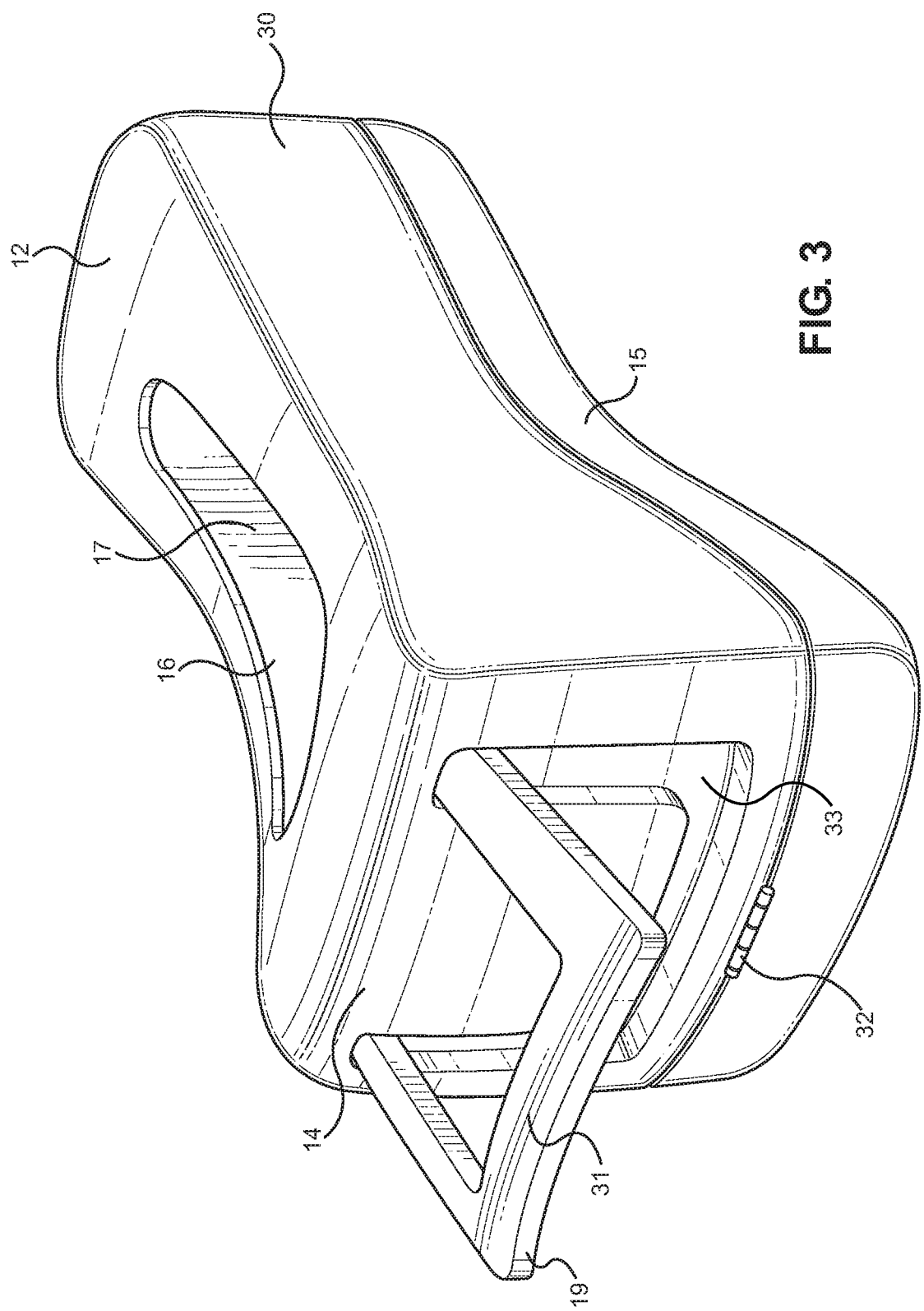
FIG. 3 shows a perspective view of an embodiment of the handle of the portable urinal.

Referring now to FIG. 3, there is shown a perspective view of an embodiment of the handle of the portable urinal. In the illustrated embodiment, a handle 19 is disposed on the back side 14 of the container 11. The handle 19 has an outer side 31 In the illustrated embodiment, the handle 19 is hingedly attached to the back side 14 of the portable urinal 11 such that it has a first position and a second position. In the illustrated embodiment, the container 11 comprises a recess 33 disposed on the back side 14 adapted to fit the handle 19. The outer side 31 of handle 19 is flush with the back side 14 in the first position so as to provide a compact form factor. In some embodiments, the handle 19 is disposed along the front side 21.

Figure 4:
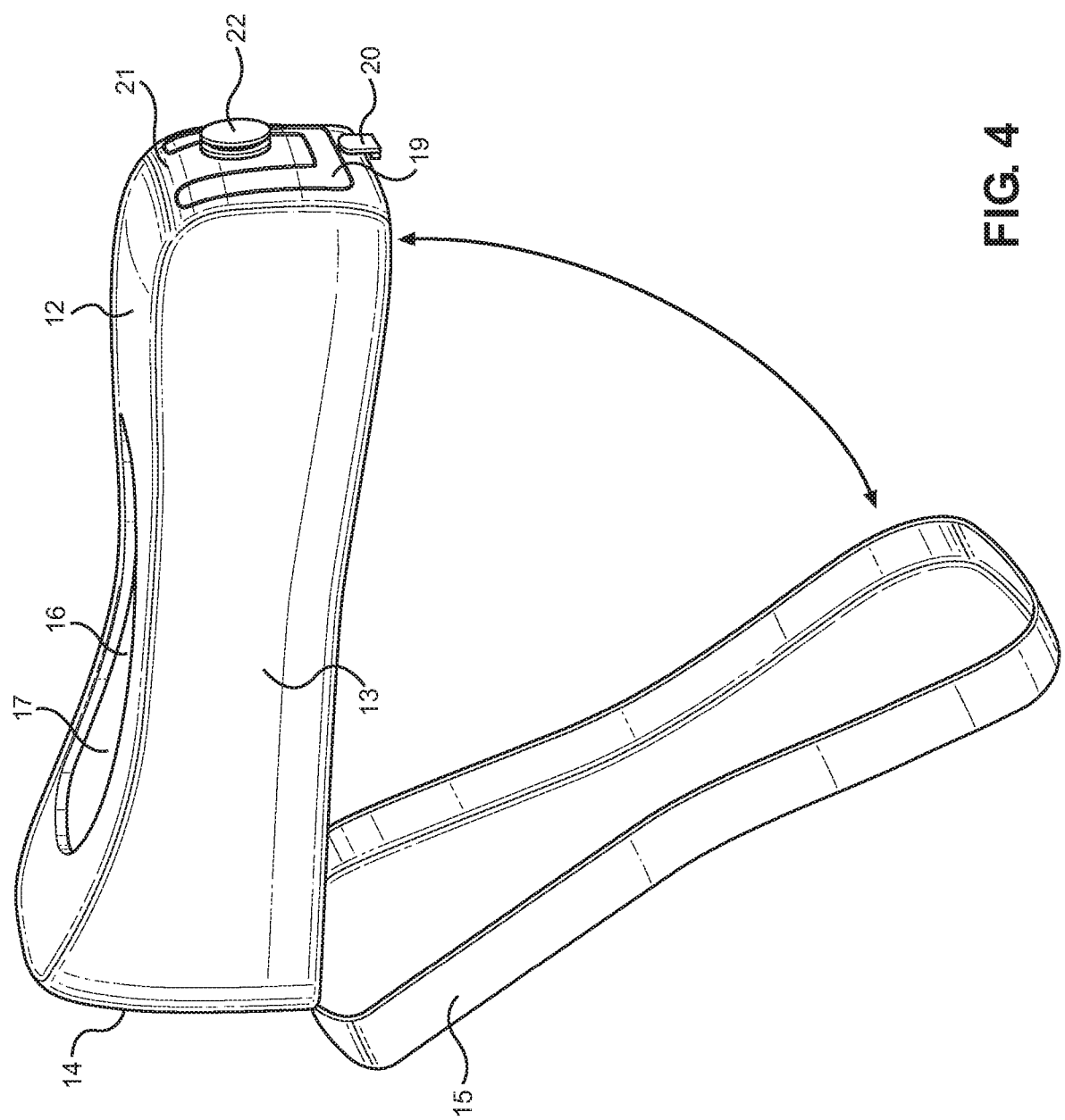
FIG. 4 shows a perspective view of an embodiment of the portable urinal.

Referring to FIG. 4, there is shown a perspective view of an embodiment of the portable urinal. In the illustrated embodiment, the base 15 is hingedly connected along the back side 14 at a hinge 32. The base 15 is maintained in its closed position via a latch 20 disposed along the front side 21 of the portable urinal 11. In its closed position, the base 15 is adapted to be watertight. In other embodiments, the latch 20 and hinge 32 are disposed along the back side 14 and the front side 21, respectively. In the illustrated embodiment, the handle 19 is disposed along the front side 21 and in its first position such that the outer side 31 is flush with the front side 21. The cap 22 is removably secured to the spout 18 in its collapsed position such that the spout 18 is flush with the front side 21.

In one use, the portable urinal 11 is closed such that the base 15 is secured via the latch 20 and the cap 22 is engaged with the spout 18 to form a watertight seal. The user would grasp the first and second sidewalls 13, 30 with their thighs and urinate through the aperture 16 into the interior volume 17. To empty the interior volume 17, the user would extend the spout 18 to its extended position and remove the cap 22. The portable urinal 11 would then be upturned, either via gripping the handle 19 or by grasping the portable urinal 11 itself, such that the urine contained within the interior volume 17 would be evacuated. When emptied, the user can then open the portable urinal 11 by triggering the latch 20 and lowering the base 15 about the hinge 32. This opening allows for access to the interior volume 17 for cleaning purposes. The user would then close the portable urinal 11 and continue carrying the portable urinal 11 by the handle 19.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A portable female urinal, comprising:
a container including a front end, a rear end, and a pair of opposing lateral sidewalls extending therebetween;
wherein the pair of opposing lateral sidewalls taper inwards from the front end and the rear end, such that an exterior surface of each of the pair of opposing lateral sidewalls is concave;
wherein a base is hingedly attached to the container along a back side of the container;
wherein an entirety of an upper edge of a wall extending upwardly away from a perimeter of the base is in contact with an entirety of a lower edge of the sidewall when the base is in a closed position;
an aperture configured to receive urine therethrough disposed within an upper end;
wherein the aperture is defined by a lip extending inwardly from an upper edge of each of the front end, rear end, and the pair of opposing sidewalls;
wherein the aperture tapers from a rear side thereof towards a front side thereof; and
a spout disposed on a front side, the spout configured for telescopic movement between an extended position and a collapsed position.

2. The portable female urinal of claim 1, wherein a watertight seal is formed between the upper edge and the lower edge when the base is in the closed position.

3. The portable female urinal of claim 1, wherein the spout is adapted to rest flush with the front side of the container when in the collapsed position.

4. The portable female urinal of claim 1, further comprising a cap adapted to removably secure to the spout.

5. The portable female urinal of claim 1, wherein a base is hingedly attached to the container along a back side of the container.

6. The portable female urinal of claim 1, further comprising a latch disposed on the front side adapted to removably secure the base to the container.

7. The portable female urinal of claim 1, wherein the spout is in fluid communication with an interior volume of the container, the spout adapted to dispense fluid therefrom.

8. The portable female urinal of claim 1, wherein an upper side of the container comprises an arcuate shape tapering inwardly from the front end and the rear end.

9. The portable female urinal of claim 1, wherein the rear end comprises a height greater than that of the front end.

10. The portable female urinal of claim 1, further comprising a handle hingedly attached to the container, wherein the handle is selectively movable between a first position and a second position.

11. The portable female urinal of claim 10, wherein the handle is disposed on a back side of the container.

12. The portable female urinal of claim 10, wherein the handle is disposed on the front side.

13. The portable female urinal of claim 10, wherein the handle is disposed within a recess of the container, such that an entirety of an outer side of the handle is flush with an exterior of the container when the handle is in the first position.

14. The portable female urinal of claim 13, wherein the recess comprises the same cross-section as that of the handle, such that the exterior of the container is continuous when the handle is in the first position.

* * * * *